US012594430B2

(12) United States Patent
Peichel et al.

(10) Patent No.: US 12,594,430 B2
(45) Date of Patent: Apr. 7, 2026

(54) TEMPERATURE SENSING OF IMPLANTED WIRELESS RECHARGE COIL

(71) Applicant: Boston Scientific Scimed, Inc., Maple Grove, MN (US)

(72) Inventors: David J. Peichel, Minneapolis, MN (US); Pankti N. Shah, Minneapolis, MN (US); Joel B. Artmann, Elk River, MN (US); Jonathan P. Roberts, Coon Rapids, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1166 days.

(21) Appl. No.: 17/140,655

(22) Filed: Jan. 4, 2021

(65) Prior Publication Data
US 2022/0212018 A1 Jul. 7, 2022

(51) Int. Cl.
| | |
|---|---|
| *A61N 1/372* | (2006.01) |
| *A61N 1/378* | (2006.01) |
| *G01K 1/024* | (2021.01) |
| *G01K 3/00* | (2006.01) |
| *G01K 7/00* | (2006.01) |
| *G08C 17/02* | (2006.01) |
| *H02J 7/02* | (2016.01) |
| *H02J 50/12* | (2016.01) |
| *H02J 50/80* | (2016.01) |
| *H02J 50/90* | (2016.01) |

(52) U.S. Cl.
CPC ....... *A61N 1/37217* (2013.01); *A61N 1/3787* (2013.01); *G08C 17/02* (2013.01); *H02J 50/80* (2016.02); *G01K 7/00* (2013.01)

(58) Field of Classification Search
CPC .. A61N 1/37217; A61N 1/3787; G01K 1/024; G01K 3/005; G01K 7/00; G08C 17/02; H02J 2310/23; H02J 50/12; H02J 50/80; H02J 50/90; H02J 7/02
USPC ....................................... 607/1–95, 115–156
See application file for complete search history.

(56) References Cited

U.S. PATENT DOCUMENTS

| | | | |
|---|---|---|---|
| 7,997,854 | B2 | 8/2011 | LaRose et al. |
| 8,419,609 | B2 | 4/2013 | Shambaugh, Jr. et al. |
| 10,143,788 | B2 | 12/2018 | Rudser et al. |

(Continued)

FOREIGN PATENT DOCUMENTS

WO 2017021846 A1 2/2017

*Primary Examiner* — Benjamin J Klein
*Assistant Examiner* — Vynn V Huh
(74) *Attorney, Agent, or Firm* — Seager, Tufte & Wickhem LLP

(57) ABSTRACT

The present disclosure provides a transcutaneous energy transfer system (TETS), having an implantable receiving coil in communication with an implantable controller and a hermetically sealed package encased by the implantable receiving coil. The hermetically sealed package including a plurality of tuning capacitors, at least one temperature sensor, scavenging circuitry configured to scavenge power from the plurality of tuning capacitors, and a temperature measuring circuit in communication with the at least one temperature sensor and the scavenging circuitry. The at least one temperature sensor being configured to measure a temperature of the hermetically sealed package and the temperature measuring circuit being configured to transmit the measured temperature to the implantable controller.

20 Claims, 4 Drawing Sheets

(56)          References Cited

U.S. PATENT DOCUMENTS

2002/0198582 A1 *  12/2002  Edell ........................ A61N 1/05
                                                              607/116
2003/0114897 A1 *   6/2003  Von Arx  ............ A61N 1/37276
                                                              607/60
2009/0284220 A1 *  11/2009  Toncich  ............... H01Q 1/2225
                                                              320/108
2010/0106223 A1 *   4/2010  Grevious  ........... A61N 1/37229
                                                              343/866
2011/0245892 A1 *  10/2011  Kast  .................... A61N 1/3787
                                                              29/600
2013/0289662 A1 *  10/2013  Olson  ................. A61N 1/3787
                                                              607/61

* cited by examiner

TEMPERATURE SENSING OF IMPLANTED WIRELESS RECHARGE COIL

CROSS-REFERENCE TO RELATED APPLICATION n/a.

FIELD

The present technology is generally related to a system for measuring temperature in a transcutaneous energy transfer system (TETS).

BACKGROUND

Many implantable medical devices have significant energy requirements. A transcutaneous energy transfer system ("TETS") may be used to power implantable devices including artificial hearts, defibrillators, and electrical systems. Generally, a TETS can transfer energy from an external transmission coil to a receiving coil that is implanted under the skin. A TETS may be used to supplement, replace, or charge an implanted power source such as a rechargeable battery. Using a TETS to power these vital implantable devices can significantly lessen the potential of infection as the TETS does not require constant puncturing of the skin and/or wires that pass through the skin. Also, a patient may have increased mobility with the implantable device as power may be transmitted over a range of skin thicknesses.

Proper alignment of the external transmission coil and the implanted receiving coil is critical to transfer energy from the external transmission coil to the receiving coil through an area of the skin that separates the two coils. If sufficient alignment is not maintained between these two coils, interrupted operation of the implanted medical device may occur. Patient movement may cause the position of the external transmission coil and the receiving coil to shift and not be properly positioned to allow for the desired or required transfer of energy to power the implantable device and/or recharge an implantable battery. Misalignment between the external transmission coil and the receiving coil may further result in undesirable heating of the receiving coil.

SUMMARY

The techniques of this disclosure generally relate to implantable blood pumps, and in particular, measuring temperature during power transfer.

In one aspect, the present disclosure provides a transcutaneous energy transfer system (TETS) having an implantable receiving coil in communication with an implantable controller and a hermetically sealed package encased by the implantable receiving coil. The hermetically sealed package including a plurality of tuning capacitors and at least one temperature sensor. The at least one temperature sensor being configured to measure a temperature of the hermetically sealed package. The hermetically sealed package further including scavenging circuitry configured to scavenge power from the plurality of tuning capacitors and a temperature measuring circuit in communication with the at least one temperature sensor and the scavenging circuitry. The temperature measuring circuit being configured to transmit the measured temperature to the implantable controller.

In another aspect of this embodiment, the implantable receiving coil is configured for transcutaneous inductive communication with an external transmission coil.

In another aspect of this embodiment, the measured temperature of the hermetically sealed package is indicative of a degree of alignment between the hermetically sealed package and the external transmission coil.

In another aspect of this embodiment, one selected from the group consisting of at least one connector and at least one cable extends from the implantable receiving coil to the implantable controller.

In another aspect of this embodiment, the measured temperature is transmitted on an RF modulated carrier signal through the one selected from the group consisting of the at least one connector and the at least one cable.

In another aspect of this embodiment, a frequency of the RF modulated carrier signal is higher than a power transfer frequency between the implantable receiving coil and the external transmission coil.

In another aspect of this embodiment, an external controller in communication with the external transmission coil, the implantable controller being configured to perform at least one operation selected from the group consisting of: reduce battery charging, disable battery charging, and transmit an alert to the external controller, when the measured temperature of the hermetically sealed package exceeds a predetermined threshold temperature.

In another aspect of this embodiment, the predetermined threshold temperature is a temperature between 43° C. and 65° C.

In another aspect of this embodiment, the alert is at least one selected from the group consisting of an audible alert notification, a visual alert notification, and a tactile alert notification to correct the degree of alignment between the implantable receiving coil and the external transmission coil.

In another aspect of this embodiment, the hermetically sealed package is composed of at least one selected from the group consisting of titanium, glass, sapphire and ceramic materials.

In another aspect of this embodiment, the alert is transmitted from the implantable controller to the external controller via a Bluetooth signal.

In one aspect, a transcutaneous energy transfer system (TETS), comprises an external transmission coil in communication with an external controller and an implantable receiving coil in communication with an implantable controller. The implantable receiving coil being configured for transcutaneous inductive communication with the external transmission coil and the implantable controller being configured to receive power from the implantable receiving coil. The TETS further including a hermetically sealed package encased by the implantable receiving coil. The hermetically sealed package including a plurality of tuning capacitors and at least one temperature sensor. The at least one temperature sensor being configured to measure a temperature of the hermetically sealed package. The hermetically sealed package further including scavenging circuitry configured to scavenge power from the plurality of tuning capacitors and a temperature measuring circuit in communication with the at least one temperature sensor and the scavenging circuitry. The temperature measuring circuit being configured to transmit the measured temperature to the implantable controller.

In another aspect of this embodiment, the measured temperature of the hermetically sealed package is indicative of a degree of alignment between the hermetically sealed package and the external transmission coil.

3

In another aspect of this embodiment, one selected from the group consisting of at least one connector and at least one cable extends from the implantable receiving coil to the implantable controller.

In another aspect of this embodiment, the measured temperature is transmitted on an RF modulated carrier signal through the one selected from the group consisting of the at least one connector and the at least one cable.

In another aspect of this embodiment, the implantable controller is configured to perform at least one operation selected from the group consisting of: reduce battery charging, disable battery charging, and transmit an alert to the external controller, when the measured temperature of the hermetically sealed package exceeds a predetermined threshold temperature.

In another aspect of this embodiment, the predetermined threshold temperature is a temperature between 43° C. and 65° C.

In another aspect of this embodiment, the alert is at least one selected from the group consisting of an audible alert notification, a visual alert notification, and a tactile alert notification to correct the degree of alignment between the implanted receiving coil and the external transmission coil.

In another aspect of this embodiment, a frequency of the RF modulated carrier signal is higher than a power transfer frequency between the implantable receiving coil and the external transmission coil.

In one aspect, a transcutaneous energy transfer system (TETS) includes an external transmission coil in communication with an external controller, an implantable receiving coil in communication with an implantable controller, and a hermetically sealed package encased by the implantable receiving coil. The implantable receiving coil being configured for transcutaneous inductive communication with the external transmission coil and the implantable controller being configured to receive power from the implantable receiving coil. The hermetically sealed package being composed of at least one selected from the group consisting of glass, titanium, sapphire, and ceramic materials. The hermetically sealed package including a plurality of tuning capacitors, scavenging circuitry, a temperature measuring circuit, and at least one temperature sensor being configured to measure a temperature of the hermetically sealed package. The measured temperature of the hermetically sealed package being indicative of a degree of alignment between the implantable receiving coil and the external transmission coil. The scavenging circuitry being configured to scavenge power from the plurality of tuning capacitors. The temperature measuring circuit being in communication with the at least one temperature sensor and the scavenging circuitry. The temperature measuring circuit being configured to transmit the measured temperature to the implanted controller on an RF modulated carrier signal through one selected from the group consisting of at least one connector and at least one cable. The RF modulated carrier signal having at least one frequency band selected from the group consisting of ISM frequency bands and MICS frequency bands. The selected at least one frequency band being higher than a power transfer frequency between the implantable receiving coil and the external transmission coil. The implantable controller being further configured to perform at least one operation selected from the group consisting of: reduce battery charging, disable battery charging, and transmit an alert to the external controller, when the measured temperature of the hermetically sealed package exceeds a predetermined threshold temperature between 43° C. and 65° C. The alert being at least one selected from the group consisting of an audible alert notification, a visual alert notification, and a tactile alert notification to correct the degree of alignment between the implanted receiving coil and the external transmission coil.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
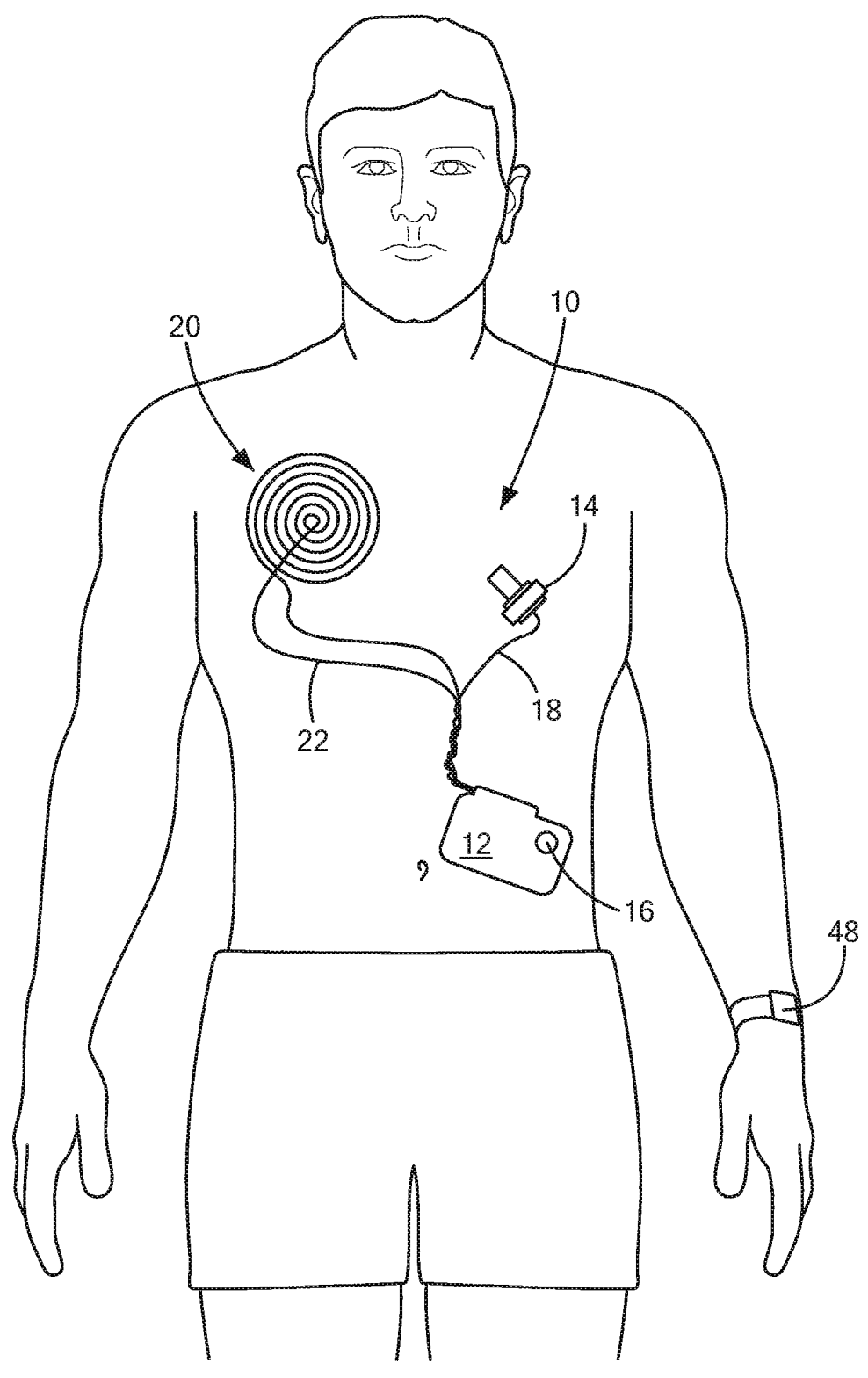
FIG. 1 is an internal system view of an implantable blood pump with a TETS receiver source constructed in accordance with the principles of the present application.

Referring now to the drawings in which like reference designators refer to like elements there is shown in FIGS. 1 and 2 an exemplary transcutaneous energy transfer system ("TETS") constructed in accordance with the principles of the present application and designated generally as "10." The TETS 10 may be fully implantable within a patient, whether human or animal, which is to say there are no percutaneous connections between the implanted components of the TETS 10 and the components outside of the body of the patient. In the configuration shown in FIG. 1, the TETS 10 includes an implantable controller 12 implanted within the body of the patient. The implantable controller 12 includes a control circuit having processing circuitry configured to control operation of an implantable blood pump 14. The implantable controller 12 may include an internal power source 16, configured to power the components of the implantable controller 12 and provide power to one or more implantable medical devices, for example, the implantable blood pump, such as a ventricular assist device ("VAD") 14 implanted within the left ventricle of the patient's heart. The power source 16 may include a variety of different types of power sources including an implantable battery. VADs 14 may include centrifugal pumps, axial pumps, or other kinds electromagnetic pumps configured to pump blood from the heart to blood vessels to circulate around the body. One such centrifugal pump is the HVAD and is shown and described in U.S. Pat. No. 7,997,854, the entirety of which is incorporated by reference. One such axial pump is the MVAD and is shown and described in U.S. Pat. No. 8,419,609, the entirety of which is incorporated herein by reference. In an exemplary configuration, the VAD 14 is electrically coupled to the implantable controller 12 by one or more implanted conductors 18 configured to provide power to the VAD 14, relay one or more measured feedback signals from the VAD 14, and/or provide operating instructions to the VAD 14.

Figure 2:
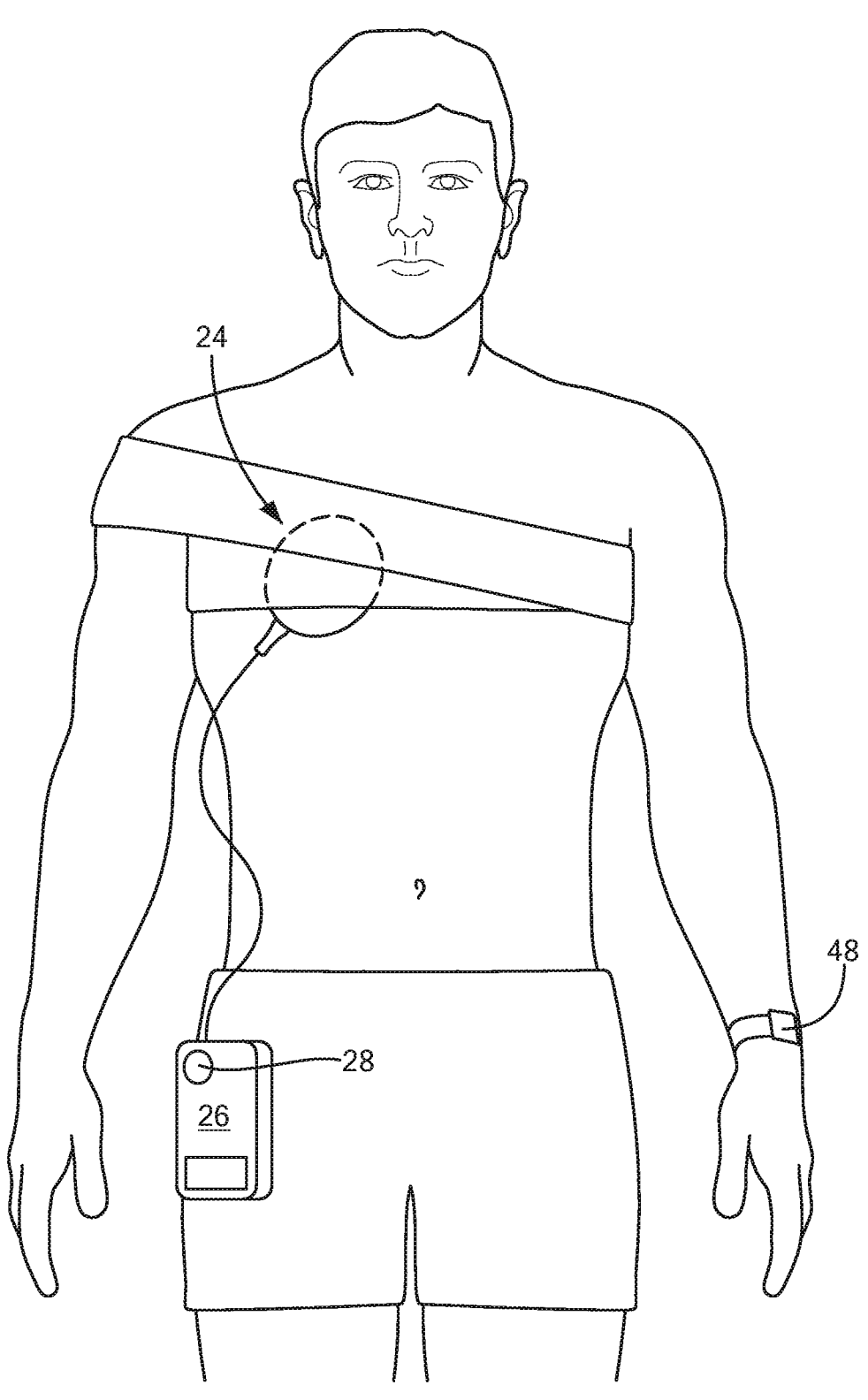
FIG. 2 is an external view of a TETS transmitter, and a controller of the system shown in FIG. 1.

Continuing to refer to FIG. 1, an implantable receiving coil 20 may be coupled to the implantable controller 12 by, for example, at least one connector and/or cable 22. In an exemplary configuration, the receiving coil 20 may be implanted subcutaneously proximate the thoracic cavity, although any subcutaneous position may be utilized for implanting the receiving coil 20. The receiving coil 20 is configured to be inductively powered through the patient's skin by an external transmission coil 24 (seen in FIG. 2) disposed opposite the receiving coil 20 on the outside/ exterior of the patient's body. As shown in FIG. 2, the transmission coil 24 may be coupled to an external controller 26 having a power source 28 such as, for example, a portable battery carried by the patient or wall power. In one configuration, the battery is configured to generate a radiofrequency signal for transmission of energy from the transmission coil 24 to the receiving coil 20. The receiving coil 20 may be configured for transcutaneous inductive communication with the transmission coil 24.

Figure 3:
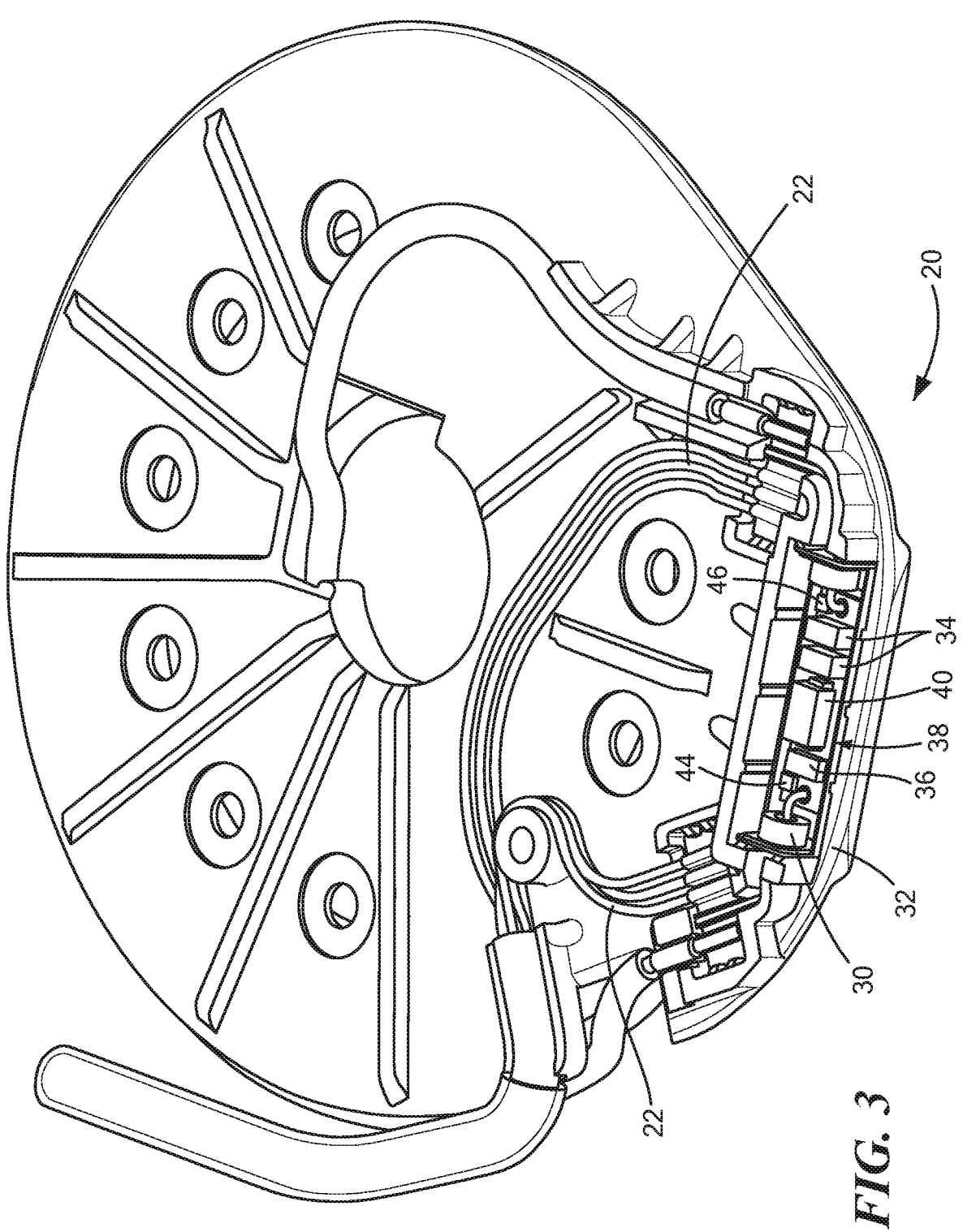
FIG. 3 is a perspective view of an implantable receiving coil of the system as show in FIGS. 1 and 2.

Referring now to FIG. 3, the implantable receiving coil 20 is shown. The receiving coil 20 includes a hermetically sealed package 30 encased by an exterior surface 32 of the receiving coil 20. The hermetically sealed package 30 includes a plurality of tuning capacitors 34, at least one temperature sensor 36, and a temperature measuring circuit 40, disposed on a circuit board 38. The receiving coil 20 further includes a transient voltage suppression (TVS) diode (not shown) disposed within the hermetically sealed package 30 to protect the implantable receiving coil 20 from spikes in voltage that may occur during the power transfer phase. The at least one temperature sensor 36 is configured to measure the temperature of the hermetically sealed package

30 during a power transfer phase between the transmission coil 24 and the receiving coil 20 wherein the internal power source 16 is charged.

Figure 4:
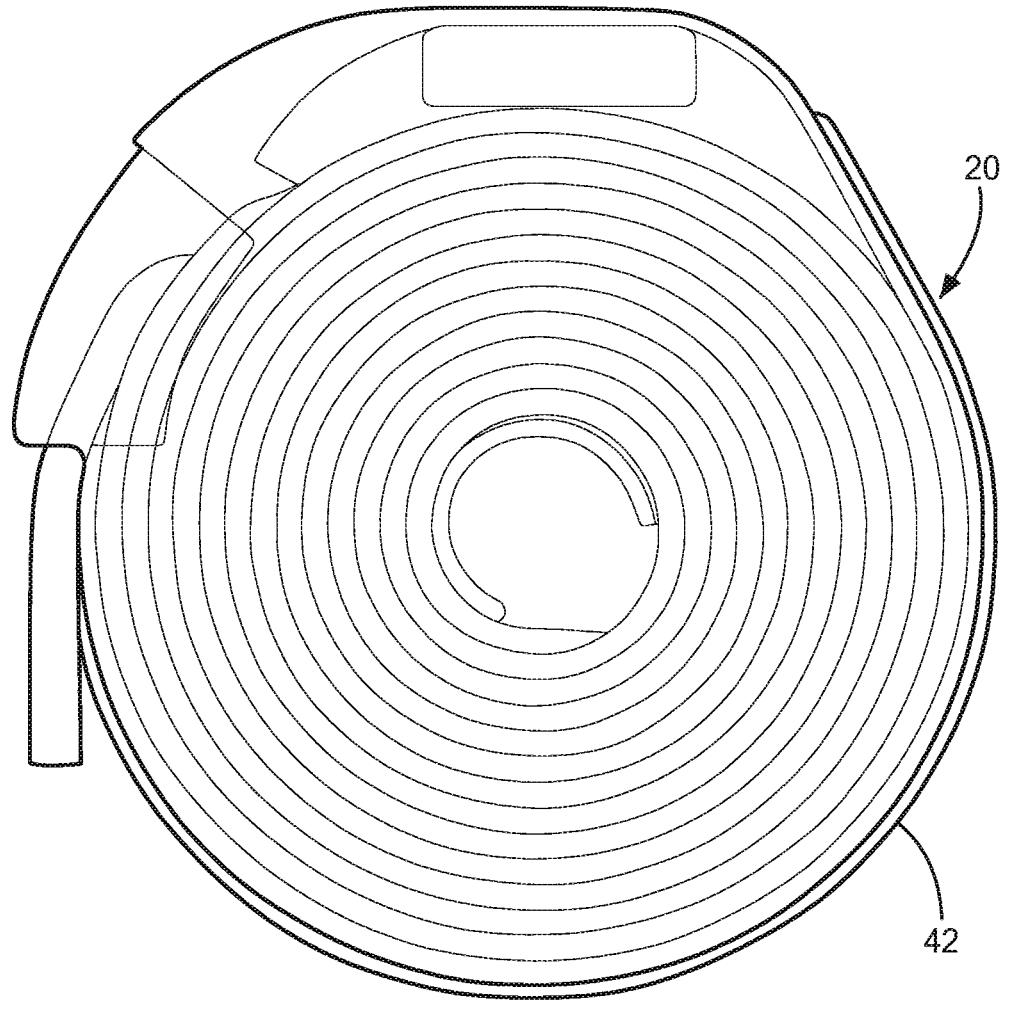
FIG. 4 is a top view of a silicone housing that encompasses the implantable receiving coil of FIG. 3.

As a non-limiting example, the hermetically sealed package 30 may be composed of glass, ceramic materials, titanium, sapphire, or any other type of metal with conductive properties that would protect the components contained within the hermetically sealed package 30 from corrosion. Excess heating of the hermetically sealed package 30 may result from a misalignment between the receiving coil 20 and transmission coil 24 during charging of the internal power source 16. Increased eddy current heating may also affect the temperature of the receiving coil's 20 silicone housing 42 (as shown in FIG. 4) which can lead to discomfort or harm to the patient. To protect the patient from discomfort or harm, the at least one temperature sensor 36 continuously and/or periodically measures the temperature of the hermetically sealed package 30.

Continuing to refer to FIG. 3, the receiving coil 20 further includes scavenging circuitry 44 encased within the hermetically sealed package 30. The scavenging circuitry 44 and the temperature measuring circuit 40 are in communication with the at least one temperature sensor 36 and the plurality of tuning capacitors 34. The scavenging circuitry 44 scavenges power from the AC voltage present across the plurality of tuning capacitors 34 and converts the AC voltage to DC voltage in order to power the temperature measuring circuit 40 and Radio Frequency (RF) modulating circuitry (not shown). Once powered, the temperature measuring circuit 40 then transmits the measured temperature to the implantable controller 12 via a radio antenna, transducer, transmitter, receiver, transceiver 46, or the like by modulating the data on an RF modulated carrier signal via the RF modulating frequency and coupling the carrier signal to the at least one connector and/or cable 22 extending between the receiving coil 20 and the implantable controller 12. The carrier frequency of the RF modulated carrier signal may be higher than a power transfer frequency between the receiving coil 20 and the transmission coil 24 so that the temperature signal does not interfere with charging of the internal power source 16. In one exemplary embodiment, the carrier frequency is a frequency selected from the following: 13.56 MHz, 433 MHz, 900 MHz, or 2.4 GHz and may be sent using a unidirectional or bidirectional communication channel. Additionally, the implantable controller 12 may also have an antenna, transducer, transmitter, receiver, transceiver, or the like to receive the temperature signal from the receiving coil 20. After receiving the temperature signal, the implantable controller 12 then compares the measured temperature of the hermetically sealed package 30 against a predetermined threshold temperature. Further, the carrier signal may also be wirelessly transmitted to an external radio (not shown) in the external transmission coil 24 and then wirelessly relayed to the external controller 26 from the external radio of the transmission coil 24.

Additionally, it should be noted that although FIG. 3 illustrates the plurality of tuning capacitors 34, at least one temperature sensor 36, temperature measuring circuit 40, scavenging circuitry 44, and transceiver 46 as being located within the hermetically sealed package 30, any or all of these components may also be disposed outside of the hermetically sealed package 30 if desired by a clinician.

Now referring to FIGS. 3-4, in an exemplary embodiment, it may be preferable to keep the temperature of the silicone housing 42 below 43° C. Temperatures of the silicone housing 42 above 43° C. may result in discomfort or harm to the patient. Additionally, due to the difference in thermal resistance between the hermetically sealed package 30 and the silicone housing 42, the temperature of the hermetically sealed package 30 may be higher than 43° C. when the temperature of the silicone housing 42 is 43° C. For example, the hermetically sealed package 30 may have a measured temperature between 43° C. and 65° C. when the silicone housing 42 has a temperature around 43° C. As such, the predetermined threshold temperature may be a temperature between 43° C. and 65° C. depending on the level of thermal resistance between the hermetically sealed package 30 and the surface of the silicone housing 42.

The implantable controller 12 is configured to generate at least one alert if the measured temperature of the hermetically sealed package 30 is greater than the predetermined threshold temperature. Alternatively, the implantable controller 12 may also be configured to reduce and/or disable charging of the internal power source 16 when the temperature of the hermetically sealed package 30 exceeds the predetermined threshold temperature. The at least one alert may be at least one audible, visual, and/or tactile notification transmitted wirelessly, or along at least one cable and/or connector, via Bluetooth or radio frequency to the external controller 26 and/or an external alert device 48. Transmitting the Bluetooth or radio frequency along a cable to the external controller 26 may be a more efficient method of transmitting the signal and reduce the amount of signal loss when passing the signal through the patient's tissue. Also, clinicians may be able to further mitigate signal loss by transmitting the signals at Industrial, Scientific, and Medical (ISM) band frequencies such as, for example, 433 MHz, 6.78 MHz, 13.56 MHz, 27.12 MHz, 40.68 MHz, 915 MHz, 403.5 MHz and other similar ISM band frequencies, and/or Medical Implant Communication System (MICS) band frequencies such as, for example, 401 MHz-406 MHz. A full list of ISM frequency bands that are available to clinicians can be found in Table 1 below:

TABLE 1

| ISM Frequency Bands | | | |
|---|---|---|---|
| Frequency Range | Center Frequency | Bandwidth | Availability |
| 6.765-6.795 MHz | 6.78 MHz | 30 kHz | Locally Administered |
| 13.553-13.567 MHz | 13.56 MHz | 14 kHz | Worldwide |
| 26.957-27.283 MHz | 27.12 MHz | 326 kHz | Worldwide |
| 40.66-40.7 MHz | 40.68 MHz | 40 kHz | Worldwide |
| 433.05-434.79 MHz | 433.92 MHz | 1.74 MHz | Region 1, Locally Administered |
| 902-928 MHz | 915 MHz | 26 MHz | Region 2 (With Exceptions) |
| 2.4-2.5 GHz | 2.45 GHz | 100 MHz | Worldwide |
| 5.725-5.875 GHz | 5.8 GHz | 150 MHz | Worldwide |
| 24-24.25 GHz | 24.125 GHz | 250 MHz | Worldwide |
| 61-61.5 GHz | 61.25 GHz | 500 MHz | Locally Administered |
| 122-123 GHz | 122.5 GHz | 1 GHz | Locally Administered |
| 244-246 GHz | 245 GHz | 2 GHz | Locally Administered |

The external alert device 48 may be a smartwatch (seen in FIGS. 1-2), tablet, smartphone, display, or any other type of mobile device capable of relaying at least one audible, visual, and tactile notification to a user that the receiving coil 20 and external transmission coil 24 have become misaligned or displaced, and/or that the hermetically sealed package 30 is experiencing elevated temperature levels. Once the implantable controller 12 has reduced or disabled charging of the internal power source 16, or the user has corrected the alignment of the receiving coil 20 and transmission coil 24, the alert notification may be terminated automatically or manually by the user via the external controller 26 and/or the external alert device 48.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A transcutaneous energy transfer system (TETS), comprising:

an implantable controller including an internal power supply, the implantable controller configured to be implanted at a first location within a patient;

an implantable receiving coil configured to be implanted at a second location within a patient that is separate from the first location, the implantable receiving coil electrically coupled to the implantable controller by a cable, wherein the implantable receiving coil is configured to be inductively powered through the patient's skin by an external transmission coil disposed on the outside/exterior of the patient's body and to electrically recharge the internal power supply of the implantable controller through the cable while the implantable receiving coil is being inductively powered; and a hermetically sealed package in contact with the implantable receiving coil and coupled to the implantable controller by the cable, the hermetically sealed package including:

a plurality of tuning capacitors;

at least one temperature sensor, the at least one temperature sensor being configured to measure a temperature of the hermetically sealed package;

scavenging circuitry being configured to scavenge power from the plurality of tuning capacitors to power a temperature measuring circuit; and the temperature measuring circuit connected to the at least one temperature sensor and the scavenging circuitry, wherein the temperature measuring circuit is configured to transmit the temperature measured by the at least one temperature sensor to the implantable controller through the cable.

2. The TETS of claim 1, wherein the implantable receiving coil is configured for transcutaneous inductive communication with the external transmission coil.

3. The TETS of claim 2, wherein the temperature of the hermetically sealed package measured by the at least one temperature sensor is indicative of a degree of alignment between the implantable receiving coil and the external transmission coil.

4. The TETS of claim 1, wherein the temperature measuring circuit is further configured to transmit through the cable the temperature measured by the at least one temperature sensor on an RF modulated carrier signal.

5. The TETS of claim 4, wherein a frequency of the RF modulated carrier signal is higher than a power transfer frequency between the implantable receiving coil and the external transmission coil.

6. The TETS of claim 1, further including an external controller in communication with the external transmission coil, the implantable controller being configured to perform at least one operation selected from a group including reducing battery charging, disabling battery charging, and transmitting an alert to the external controller when the temperature measured by the at least one temperature sensor of the hermetically sealed package exceeds a predetermined threshold temperature.

7. The TETS of claim 6, wherein the predetermined threshold temperature is a temperature between 43° C. and 65° C.

8. The TETS of claim 6, wherein the alert is at least one selected from a group including an audible alert notification, a visual alert notification, and a tactile alert notification to correct a degree of alignment between the implantable receiving coil and the external transmission coil.

9. The TETS of claim 6, wherein the implantable controller is configured to transmit the alert to the external controller via a Bluetooth signal.

10. The TETS of claim 1, wherein the hermetically sealed package is composed of at least one selected from a group including titanium, glass, sapphire, and ceramic materials.

11. The TETS of claim 1, wherein the internal power supply of the implantable controller is configured to provide electrical power to one or more implantable medical devices through one or more implanted conductors, the one or more implantable medical devices positioned at one or more implant locations that are different from both the first location and the second location.

12. A transcutaneous energy transfer system (TETS), comprising:

an external transmission coil in communication with an external controller;

an implantable controller including an internal power supply, the implantable controller configured to be implanted at a first location within a patient;

an implantable receiving coil configured to be implanted at a second location within a patient that is separate from the first location, the implantable receiving coil electrically coupled to the implantable controller by a cable, wherein the implantable receiving coil is configured to be inductively powered through the patient's skin by the external transmission coil disposed on the outside/exterior of the patient's body and to electrically recharge the internal power supply of the implantable controller through the cable while the implantable receiving coil is being inductively powered; and a hermetically sealed package in contact with the implantable receiving coil and coupled to the implantable controller by the cable, the hermetically sealed package including:

a plurality of tuning capacitors;

at least one temperature sensor, the at least one temperature sensor being configured to measure a temperature of the hermetically sealed package;

scavenging circuitry being configured to scavenge power from the plurality of tuning capacitors to power a temperature measuring circuit; and the temperature measuring circuit in communication with the at least one temperature sensor and the scavenging circuitry, wherein the temperature measuring circuit is configured to transmit the temperature measured by the at least one temperature sensor to the implantable controller through the cable.

13. The TETS of claim 12, wherein the temperature of the hermetically sealed package measured by the at least one temperature sensor is indicative of a degree of alignment between the implantable receiving coil and the external transmission coil.

14. The TETS of claim 12, wherein the temperature measuring circuit is further configured to transmit through the cable the temperature measured by the at least one temperature sensor on an RF modulated carrier signal.

15. The TETS of claim 14, wherein a frequency of the RF modulated carrier signal is higher than a power transfer frequency between the implantable receiving coil and an external transmission coil.

16. The TETS of claim 12, wherein the implantable controller is configured to perform at least one operation selected from the group consisting of: reducing battery charging, disabling battery charging, and transmitting an alert to the external controller when the temperature measured by the at least one temperature sensor of the hermetically sealed package exceeds a predetermined threshold temperature.

17. The TETS of claim 16, wherein the predetermined threshold temperature is a temperature between 43° C. and 65° C.

18. The TETS of claim 16, wherein the alert is at least one selected from a group including an audible alert notification, a visual alert notification, and a tactile alert notification to correct a degree of alignment between the implantable receiving coil and the external transmission coil while the implantable receiving coil is being inductively powered by the external transmission coil.

19. The TETS of claim 12, wherein the internal power supply of the implantable controller is configured to provide electrical power to one or more implantable medical devices through one or more implanted conductors, the one or more implantable medical devices positioned at one or more implant locations that are different from both the first location and the second location.

20. A transcutaneous energy transfer system (TETS), comprising:

an external transmission coil in communication with an external controller;

an implantable controller including an internal power supply, the implantable controller configured to be implanted at a first location within a patient;

an implantable receiving coil configured to be implanted at a second location within a patient that is separate from the first location, the implantable receiving coil electrically coupled to the implantable controller by a cable, wherein the implantable receiving coil is configured to be inductively powered through the patient's skin by the external transmission coil disposed on the outside/exterior of the patient's body and to electrically recharge the internal power supply of the implantable controller through the cable while the implantable receiving coil is being inductively powered; and a hermetically sealed package in contact with the implantable receiving coil and coupled to the implantable controller by the cable, the hermetically sealed package being composed of at least one selected from a group including glass, titanium, sapphire, and ceramic materials, the hermetically sealed package including:

a plurality of tuning capacitors;

at least one temperature sensor being configured to measure a temperature of the hermetically sealed package, the temperature of the hermetically sealed package measured by the at least one temperature sensor is indicative of a degree of alignment between the implantable receiving coil and the external transmission coil;

scavenging circuitry being configured to scavenge power from the plurality of tuning capacitors to power a temperature measuring circuit; and a temperature measuring circuit in communication with the at least one temperature sensor and the scavenging circuitry, wherein the temperature measuring circuit is configured to transmit through the cable the temperature measured by the at least one temperature sensor to the implantable controller on an RF modulated carrier signal, the RF modulated carrier signal having at least one frequency band selected from the group including ISM frequency bands and MICS frequency bands, wherein the selected at least one frequency band being higher than a power transfer frequency between the implantable receiving coil and an external transmission coil, the implantable controller being further configured to perform at least one operation selected from a group including: reduce battery charging, disable battery charging, and transmit an alert to the external controller, when the temperature measured by the at least one temperature sensor of the hermetically sealed package exceeds a predetermined threshold temperature between 43° C. and 65° C., the alert being at least one selected from a group including an audible alert notification, a visual alert notification, and a tactile alert notification to correct the degree of alignment between the implantable receiving coil and the external transmission coil.

* * * * *